(12) United States Patent
May et al.

(10) Patent No.: US 8,075,574 B2
(45) Date of Patent: Dec. 13, 2011

(54) SURGICAL KNOT PUSHER AND METHOD OF USE

(75) Inventors: Thomas C. May, Wrentham, MA (US); Stuart E. Fromm, Rapid City, SD (US)

(73) Assignee: DePuy Mitek, Inc., Raynham, MA (US)

( * ) Notice: Subject to any disclaimer, the term of this patent is extended or adjusted under 35 U.S.C. 154(b) by 498 days.

(21) Appl. No.: 10/916,289

(22) Filed: Aug. 11, 2004

(65) Prior Publication Data

US 2005/0033325 A1  Feb. 10, 2005

Related U.S. Application Data

(63) Continuation of application No. 10/011,452, filed on Oct. 30, 2001, now Pat. No. 6,884,249.

(60) Provisional application No. 60/269,314, filed on Feb. 16, 2001.

(51) Int. Cl.
 A61B 17/04 (2006.01)

(52) U.S. Cl. ......................................... 606/148

(58) Field of Classification Search .................. 606/139, 606/148, 144; 289/1.5, 2, 17, 18.1
See application file for complete search history.

(56) References Cited

U.S. PATENT DOCUMENTS

| | | | | |
|---|---|---|---|---|
| 408,645 A | * | 8/1889 | Woodhouse | 289/2 |
| 2,012,776 A | | 8/1935 | Roeder | |
| 3,033,204 A | * | 5/1962 | Wood | 606/139 |
| 3,717,907 A | * | 2/1973 | Klein | 403/206 |
| 4,602,635 A | * | 7/1986 | Mulhollan et al. | 606/144 |
| 4,669,473 A | | 6/1987 | Richards et al. | |
| 4,750,492 A | | 6/1988 | Jacobs | |
| 4,836,205 A | | 6/1989 | Barrett | |
| 4,845,851 A | * | 7/1989 | Warthen | 30/140 |
| 5,084,058 A | * | 1/1992 | Li | 606/148 |
| 5,087,263 A | * | 2/1992 | Li | 606/148 |
| 5,176,691 A | | 1/1993 | Pierce | |
| 5,217,470 A | * | 6/1993 | Weston | 606/148 |
| 5,222,977 A | * | 6/1993 | Esser | 606/223 |
| 5,234,445 A | | 8/1993 | Walker et al. | |
| 5,236,232 A | * | 8/1993 | Broberg | 289/1.5 |
| 5,242,459 A | * | 9/1993 | Buelna | 606/148 |
| 5,269,791 A | | 12/1993 | Mayzels et al. | |
| 5,292,327 A | * | 3/1994 | Dodd et al. | 606/148 |
| 5,324,298 A | * | 6/1994 | Phillips et al. | 606/148 |
| 5,342,374 A | * | 8/1994 | Wan et al. | 606/148 |
| 5,391,175 A | | 2/1995 | Sharpe et al. | |
| 5,395,382 A | * | 3/1995 | DiGiovanni et al. | 606/148 |
| 5,397,326 A | * | 3/1995 | Mangum | 606/148 |
| 5,403,330 A | * | 4/1995 | Tuason | 606/148 |
| 5,405,352 A | * | 4/1995 | Weston | 606/148 |
| 5,423,837 A | * | 6/1995 | Mericle et al. | 606/148 |

(Continued)

FOREIGN PATENT DOCUMENTS

AT  361026 T  5/2007

(Continued)

*Primary Examiner* — Gary Jackson
*Assistant Examiner* — Erin Colello

(57) ABSTRACT

A surgical knot pusher device allows a prepared knot to be pushed down a length of suture without deforming or collapsing the knot. The surgical knot pusher device includes a handle portion and an elongate body extending from the handle portion. The elongate body has a curved tip that is tapered and has a groove along a length of the tip. The tip also includes a central channel extending from the groove to a distal end of the tip.

13 Claims, 11 Drawing Sheets

U.S. PATENT DOCUMENTS

| | | | |
|---|---|---|---|
| 5,499,991 A * | 3/1996 | Garman et al. | 606/148 |
| 5,500,000 A | 3/1996 | Feagin et al. | |
| 5,562,684 A | 10/1996 | Kammerer | |
| 5,601,576 A | 2/1997 | Garrison | |
| 5,643,292 A * | 7/1997 | Hart | 606/144 |
| 5,653,719 A | 8/1997 | Raiken | |
| 5,681,333 A * | 10/1997 | Burkhart et al. | 606/148 |
| 5,704,943 A * | 1/1998 | Yoon et al. | 606/139 |
| 5,746,752 A | 5/1998 | Burkhart | |
| 5,746,755 A * | 5/1998 | Wood et al. | 606/148 |
| 5,752,964 A * | 5/1998 | Mericle | 606/148 |
| 5,759,189 A | 6/1998 | Ferragamo et al. | |
| 5,797,928 A * | 8/1998 | Kogasaka | 606/144 |
| 5,797,929 A | 8/1998 | Andreas et al. | |
| 5,830,220 A * | 11/1998 | Wan et al. | 606/139 |
| 5,997,555 A * | 12/1999 | Kontos | 606/148 |
| 6,045,561 A | 4/2000 | Marshall et al. | 606/148 |
| 6,117,145 A * | 9/2000 | Wood et al. | 606/148 |
| 6,132,439 A | 10/2000 | Kontos | |
| 6,143,006 A * | 11/2000 | Chan | 606/148 |
| 6,152,936 A * | 11/2000 | Christy et al. | 606/148 |
| 6,200,329 B1 * | 3/2001 | Fung et al. | 606/232 |
| 6,258,106 B1 | 7/2001 | Leonard | |
| 6,488,690 B1 * | 12/2002 | Morris et al. | 606/144 |
| 6,610,072 B1 * | 8/2003 | Christy et al. | 606/148 |
| 6,626,919 B1 * | 9/2003 | Swanstrom | 606/153 |
| 6,733,509 B2 * | 5/2004 | Nobles et al. | 606/138 |
| 6,866,673 B2 * | 3/2005 | Oren et al. | 606/148 |
| 6,884,249 B2 * | 4/2005 | May et al. | 606/148 |
| 7,094,246 B2 * | 8/2006 | Anderson et al. | 606/148 |
| 2003/0181926 A1 * | 9/2003 | Dana et al. | 606/148 |
| 2003/0204196 A1 * | 10/2003 | Bittar | 606/148 |
| 2004/0097978 A1 * | 5/2004 | Modesitt et al. | 606/148 |
| 2005/0038450 A1 * | 2/2005 | Hu et al. | 606/148 |

FOREIGN PATENT DOCUMENTS

| | | |
|---|---|---|
| AU | 200215472 | 8/2002 |
| CA | 2371418 | 2/2002 |
| DE | 509 640 | 10/1930 |
| DE | 60219840 T | 1/2008 |
| EP | 0 588 606 | 3/1994 |
| EP | 1 013 229 | 6/2000 |
| EP | 1232729 | 8/2002 |
| GB | 2 325 265 | 11/1998 |
| GB | 2 325 165 | 11/1999 |
| JP | 2002355250 | 12/2002 |
| WO | WO 95/32669 | 12/1995 |

* cited by examiner

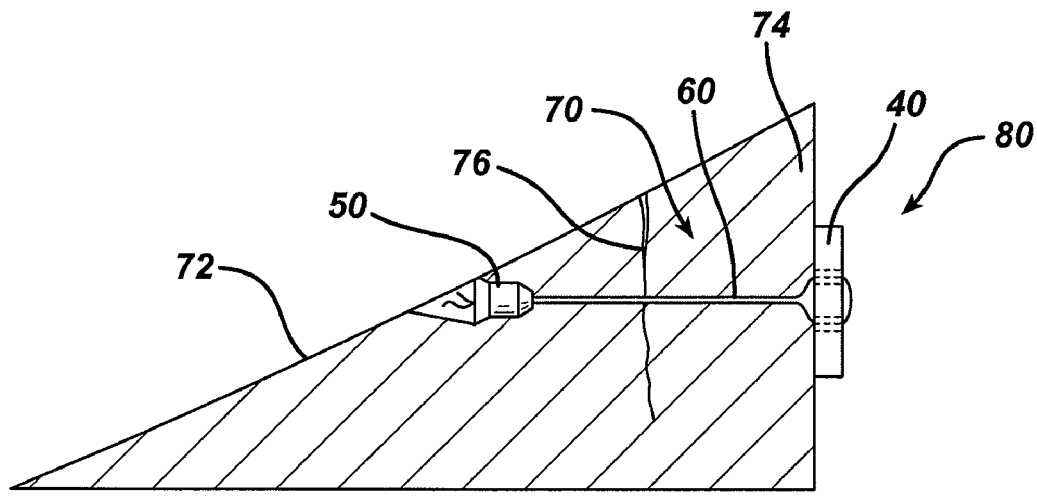
FIG. 5
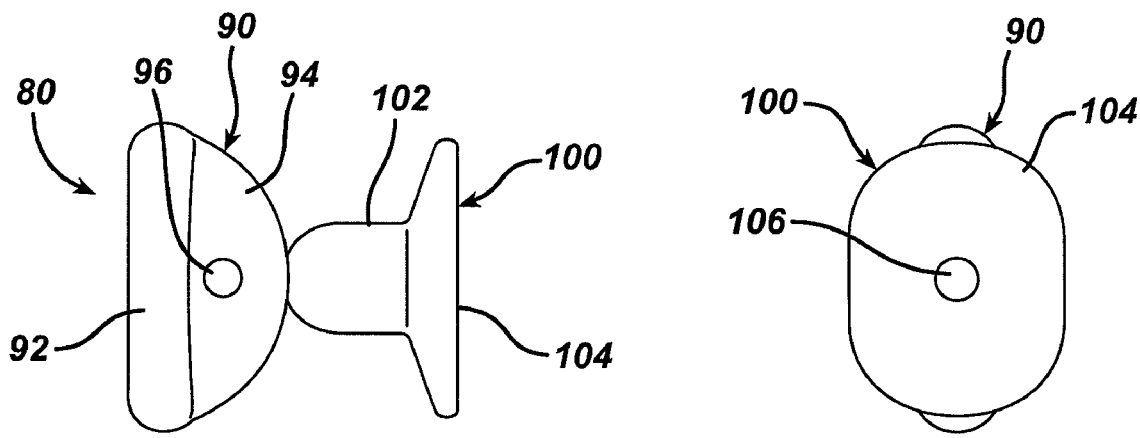
FIG. 6A  FIG. 6B

SURGICAL KNOT PUSHER AND METHOD OF USE

CROSS-REFERENCE TO RELATED APPLICATIONS

This application is a continuation of U.S. patent application Ser. No. 10/011,452 filed on Oct. 30, 2001 now U.S. Pat. No. 6,884,249 which is based on U.S. provisional application 60/269,314, filed on Feb. 16, 2001.

FIELD OF THE INVENTION

The invention relates generally to surgical tools for preparing sutures, and to methods pertaining thereto. More particularly, this invention relates to a slip knot pusher for advancing a prepared slip knot down a length of suture without deforming or collapsing the knot.

BACKGROUND OF THE INVENTION

Many surgical procedures require a knot to be tied. For example, to reattach torn tissue, a surgeon will typically form a slip knot around the detached tissue to hold the tissue in place, rather than stitch the torn tissue to the surrounding area. Formation of the slip knot requires the surgeon to manually tie a knot on the ligatures, which are long, relatively straight strands of suture material, after the ligature is threaded through the tissues to be sutured together. This procedure is often tedious and time-consuming. There is also a tendency for the slip knot to deform or collapse as the surgeon manually forces the knot down into its proper position. In addition, tying the knot in this manner is often difficult during endoscopic surgeries such as arthroscopies, where the visual field for the surgeon is severely limited by the narrow surgical area. Because of these setbacks, there exists a need for an improved method of tying a slip knot, and for surgical tools that will facilitate such a goal.

SUMMARY OF THE INVENTION

The present invention overcomes the drawbacks inherent in prior art surgical methods and devices by providing a surgical knot pusher device that allows a prepared slip knot to be pushed down a length of suture without deforming or collapsing the knot. In one embodiment, the pusher includes a handle portion and an elongate body extending from the handle portion. The elongate body has a distal tip at a distal end of the elongate body. A groove is formed in a portion of the distal tip. The tip also includes a central channel extending from the groove to a distal end of the distal tip. The distal tip may be tapered and bent with respect to the elongate body. The distal tip can be bent in a range of angles with respect to the elongate body. Alternatively, the distal tip of the surgical knot pusher device can be straight.

In one embodiment, the pusher is formed from a rigid plastic or metal. However, in another embodiment, the pusher can be formed from a malleable material that enables the surgeon to adjust the angle of the distal tip during surgery.

The surgical knot pusher device of the present invention can be used with a suture locking device for repairing soft tissue defects. The suture locking device can include a wall anchor attached to a tissue implant by a connecting suture having a preformed slip knot. In an exemplary method, the wall anchor is threaded through a soft tissue defect and placed against the outer wall of the tissue surface, with the connecting suture attached to the wall anchor extending across the defect or tear. The tissue implant can be positioned on an opposite wall of the tissue surface. The surgical knot pusher device of the present invention can then be deployed to force the preformed slip knot down the leg of the suture extending from the tissue implant and into the implant itself. The wall anchor acts as a pulley as tension is applied to the connecting suture, effecting closure of the tear and allowing the tissue implant to be pushed into the opposite wall of the tissue surface. An inserter tool comprising a cannulated needle and a push rod can be utilized to introduce the wall anchor and attached suture through the tissue defect.

Further features of the invention, its nature and various advantages will be more apparent from the accompanying drawings and the following detailed description of the drawings and the preferred embodiments.

BRIEF DESCRIPTION OF THE DRAWINGS

FIG. 5 is a perspective view of an exemplary suture locking system deployed across a soft tissue defect;

FIG. 6A is a side view of another exemplary suture locking system;

FIG. 6B is a top view of the tissue implant of FIG. 6A;

DETAILED DESCRIPTION OF THE INVENTION

Figure 1:
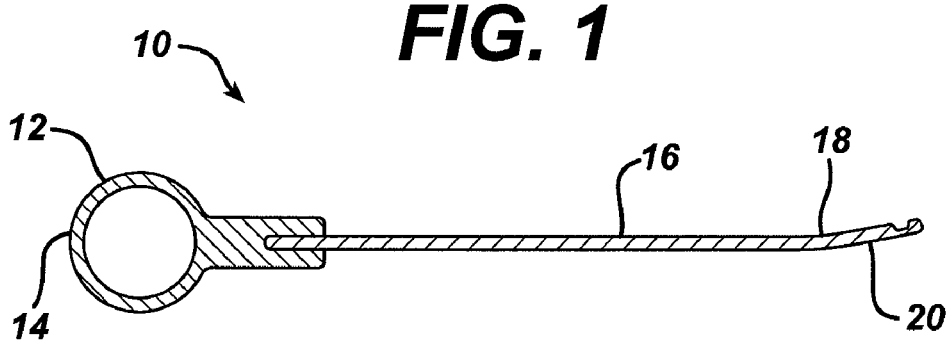
FIG. 1 is a plan view of a surgical knot pusher device of the present invention.

Referring now to the drawings and particularly to FIG. 1, a surgical knot pusher device 10 of the present invention is shown. The device 10 includes a handle portion 12 that can comprise a loop 14 for engaging a user's finger. Though handle portion 12 is illustrated with one loop 14, the handle portion 12 may include more than one loop 14 for engaging a plurality of the user's fingers. Alternatively, the handle portion 12 can comprise a gripping surface instead of loop 14. It is contemplated that the handle portion 12 can take any form commonly employed in the surgical tool art such as, e.g., a knob or grip.

Figure 2:
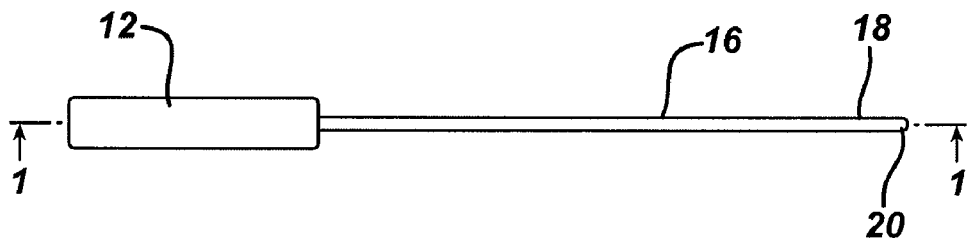
FIG. 2 is a sectional view of the surgical knot pusher device of FIG. 1 along lines A-A.

As illustrated in FIGS. 1 and 2, extending from the handle portion 12 is an elongate body 16 having a distal tip 18 at a distal end 20 of the elongate body 16. Distal tip 18 may be curved, or bent, and tapered. For example, the distal tip 18 may extend from the elongate body 16 at an angle in the range of approximately 0° to 35°. In a preferred embodiment shown in detail in FIGS. 3 and 3A, distal tip 18 extends at an angle in the range of approximately 12° to 18° from the elongate body 16. In another embodiment, distal tip 18 can extend at an angle in the range of approximately 27° to 33° with respect to elongate body 16. The bent and tapered distal tip 18 enables a surgeon to maneuver around the curvature of the patient's anatomy. For example, the bent and tapered distal tip 18 can effectively move around the curves of a bone joint, such as the condyles of the knee joint.

Figure 3:
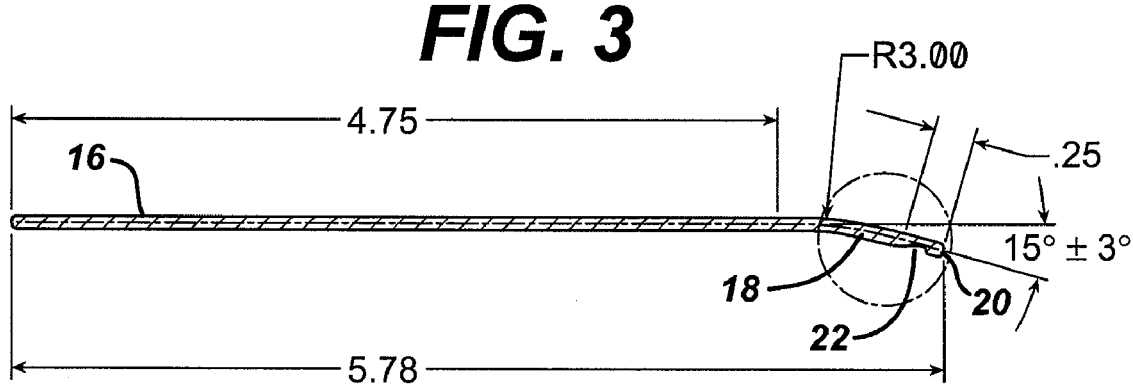
FIG. 3 is a sectional view of a portion of the device of FIG. 2.
Figure 3A:
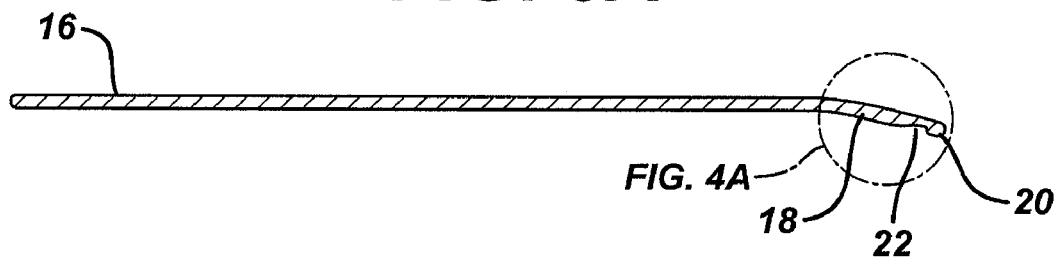
FIG. 3A is a sectional view of a portion of the device of FIG. 2 with dimension labels removed for clarity.

In one embodiment, distal tip 18 begins to bend from the elongate body 16 at about 3.00 inches from the distal end 20 of distal tip 18. Along a portion of the distal tip 18 is a dimple, or groove 22 located approximately 0.25 inches from the distal end 20 of the elongate body 16. FIGS. 3 and 3A show in detail the groove 22 having a contoured surface 24, the groove 22 being angled with respect to the surface of tip 18. Groove 22 is situated on the surface of distal tip 18 facing the bend and enables a length of suture extending out of the groove 22 to lie against the elongate body 16 without substantially increasing the overall diameter of the surgical knot pusher device 10.

Figure 4:
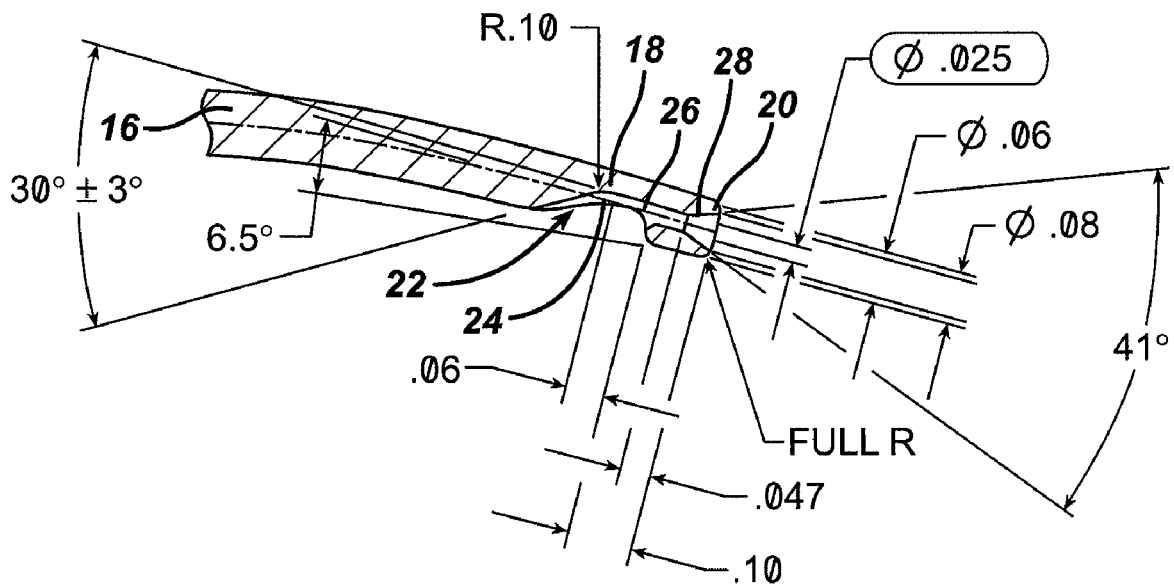
FIG. 4 is an exploded view of the distal tip of device of FIG. 1.
Figure 4A:
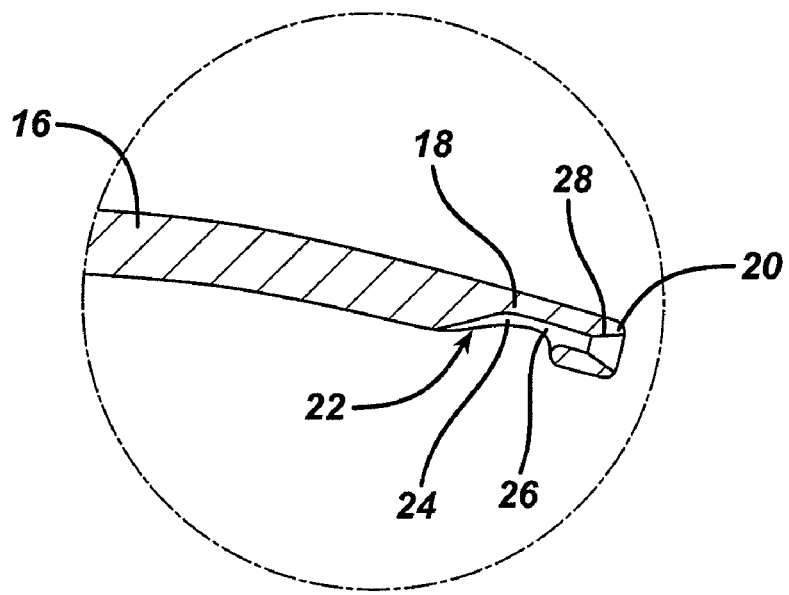
FIG. 4A is an exploded view of the distal tip of the device of FIG. 1 with dimension labels removed for clarity.

Distal tip 18 also includes a central channel 26 that runs from the groove 22 to the distal end 20 of the distal tip 18. Central channel 26 has a proximal end that is formed by a radiused wall, and channel 26 has a diameter in the range of approximately 0.025 inches, which provides sufficient clearance for a strand of suture to pass therethrough. As shown in FIGS. 4 and 4A, approximately 0.10 inches from the distal end 20, the tip 18 tapers from a 0.08 inch outer diameter to a 0.06 inch outer diameter. At this same position, central channel 26 within distal tip 18 begins to flare out to a conical opening 28 having an angle in the range of approximately 41° and a depth in the range of approximately 0.047 inches. The conical opening 28 should be of sufficient shape and dimensions to cover at least 50% of the knot intended to be pushed forward. The distal end 20 of distal tip 18 is blunt so as not to damage tissue when inserted into a patient's body.

Though illustrated with a bent distal tip 18, surgical knot pusher device 10 can also include a straight distal tip 18 that has no bend. Typically, the overall length of the surgical knot pusher device 10, including the handle 12, is in the range of about 7.5 inches, while the elongate body 16 and distal tip 18 together are in the range of about 5.78 inches long. Elongate body 16 can have a diameter in the range of about 0.093 inches. It is understood that all dimensions are merely exemplary and can be modified and altered as deemed appropriate.

Surgical knot pusher device 10 can be formed from a rigid material and can be made of either biocompatible metal or plastic. For example, device 10 may be formed of surgical grade stainless steel, titanium, or titanium alloys. However, it is contemplated that pusher 10 can be formed from a malleable metal or plastic to enable the surgeon to manually adjust the angle of the distal tip 18 as deemed appropriate. Examples of such materials include stainless steel.

Surgical knot pusher device 10 of the present invention can be used with conventional suture locking systems 80 such as shown in FIG. 5 where an outer wall anchor 40 and a tissue implant 50 are positioned on the outer wall 74 and inner wall 72, respectively, of a tissue surface 70 having a tear 76 or defect. A connecting suture 60 attached to the outer wall anchor 40 and tissue implant 50 is extended across the tear 76, the anchor 40 acting as a pulley to effect closure of the soft tissue defect 76 when force is applied to the suture 60. The suture 60 connecting outer wall anchor 40 to tissue implant 50 can be tied with a slip knot for ease in locking the suture 60.

FIGS. 6A and 6B illustrate in detail an example of a suture locking system 80 suitable for use with the device 10 of the present invention. Suture locking system 80 includes an outer wall anchor 90 and an inner wall implant 100. Outer wall anchor 90 comprises a generally cylindrical base 92 having a semi-circular flange 94 extending therefrom. A hole 96 is provided on flange 94 for attaching a suture. Outer wall anchor can have a total width in the range of about 5.0 mm and a total height in the range of about 2.5 mm. Inner wall implant 100 is shaped like a tophat and comprises a generally cylindrical base 102 having thereon a generally oval top surface 104. A through-hole 106 extends through the top surface 104 and out the cylindrical base 102 for threading a suture therethrough. Implant 100 has a total height in the range of about 1.0 mm and a width in the range of about 3.0 to 4.5 mm. Through-hole 106 is dimensioned so as to be able to firmly engage a surgical knot.

Figure 7:
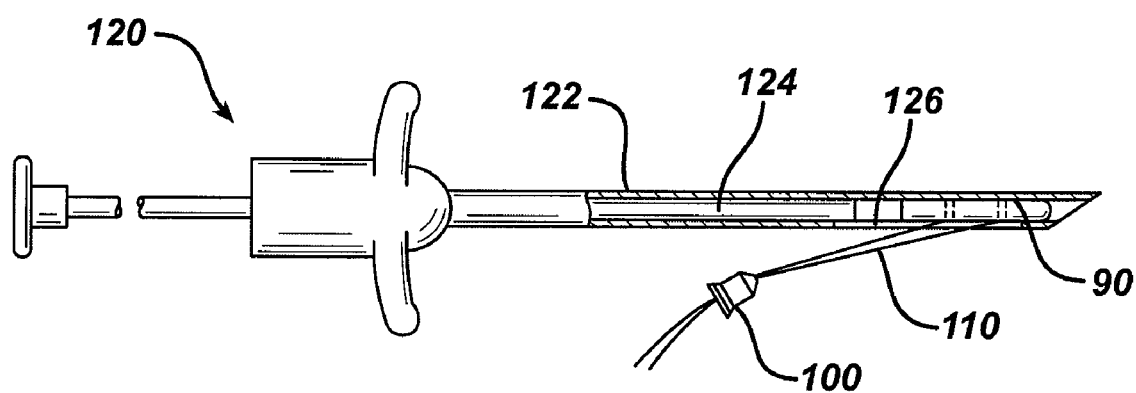
FIG. 7 is a perspective view of an inserter tool for deploying the suture locking system of FIG. 6A.

Suture locking system 80 can be deployed using inserter tool 120 illustrated in FIG. 7. Inserter tool includes a cannulated needle 122 having a push rod 124 extending therethrough. As shown, a connecting suture 110 connects anchor 90 to implant 100. The connecting suture 110 can extend into a slip knot as it exits from the through-hole 102 of the implant 100. A slot 126 on the cannulated needle 122 enables the anchor 90 to be seated within the cannulated needle 122 while the connecting suture 110 extends out of the cannulated needle 122. Implant 100, which is connected to connecting suture 110, can reside outside of the cannulated needle 122 entirely.

FIGS. 8A-8M illustrate generally a method for surgically repairing a standard repairable meniscus tear 206 using the surgical knot pusher device 10 of the present invention in combination with the suture locking system 80 described above. First, the meniscus tear 206 is evaluated and prepared in the usual manner. Then, the suture locking system 80 is preloaded onto an inserter tool 120. To effect repair of the meniscus tear 206, cannulated needle 122 of inserter tool 120 containing the outer wall anchor 90 attached by connecting suture 110 to tissue implant 100 is inserted through a standard medial or lateral portal. The needle 122 is passed through the tissue body, or meniscus 200, and into the pericapsular tissue posteriorly. Care should be taken to aim the needle away from the popliteal fossa and avoid any neurovascular injury during the procedure.

Figure 8A:
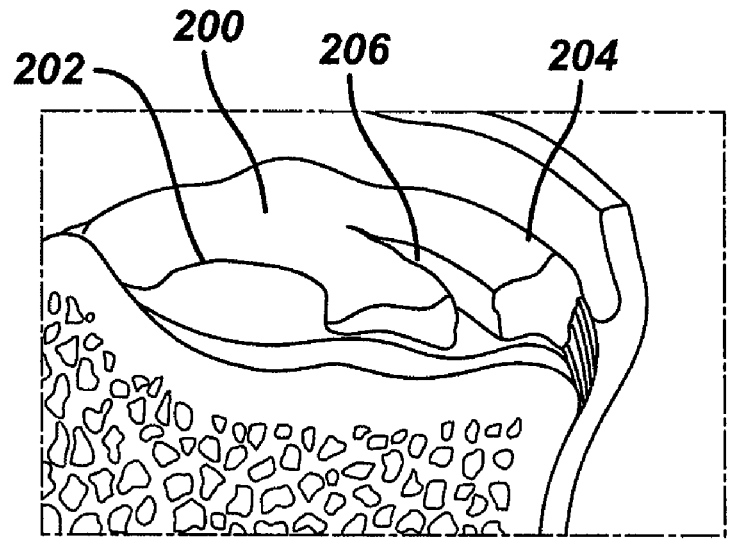
FIGS. 8A-8M depict an exemplary method of using the surgical knot pusher device and suture locking system of FIGS. 5A and 5B to repair a meniscus tear.
Figure 8B:
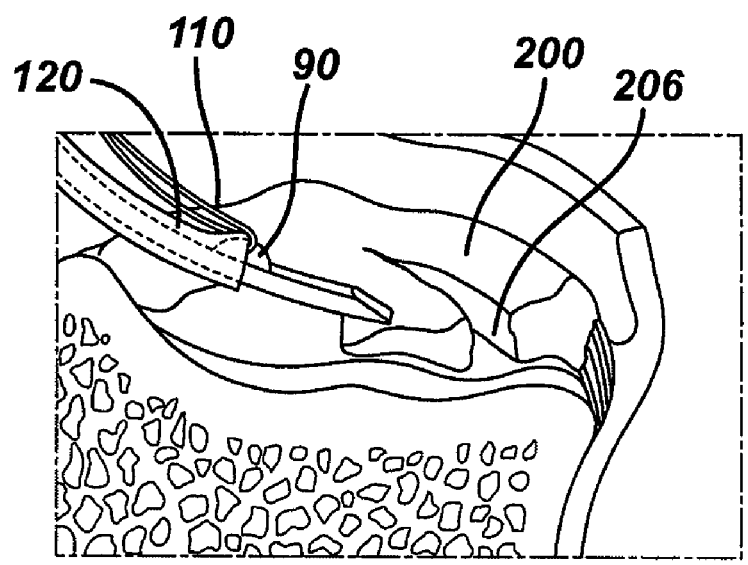
Figure 8C:
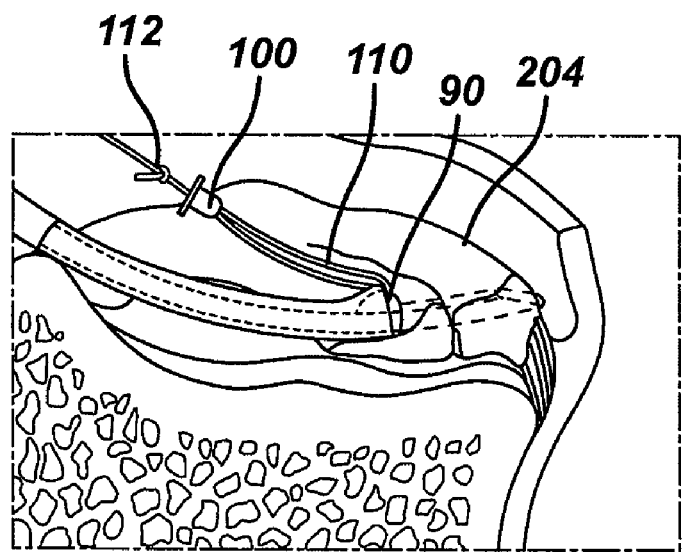
Figure 8D:
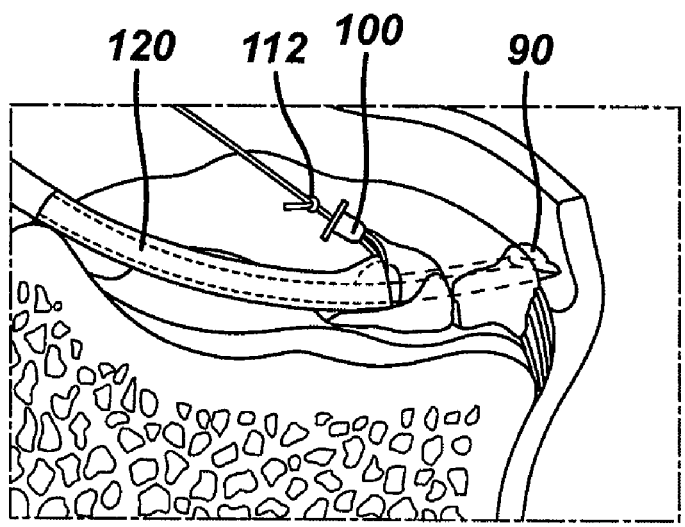
Figure 8E:
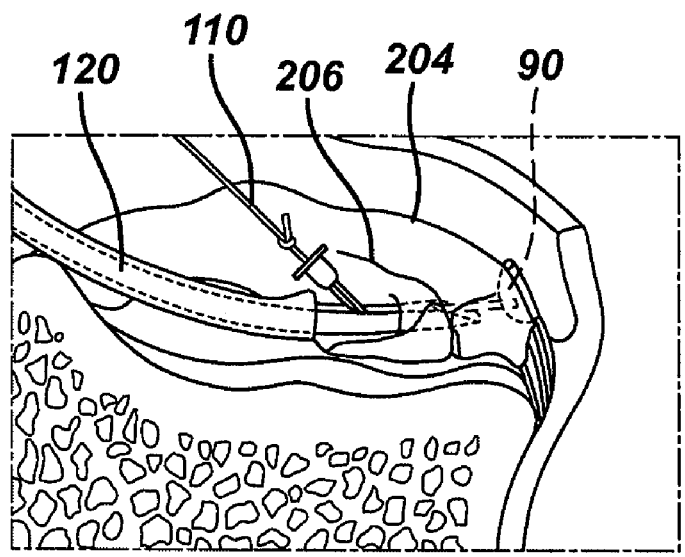
Figure 8F:
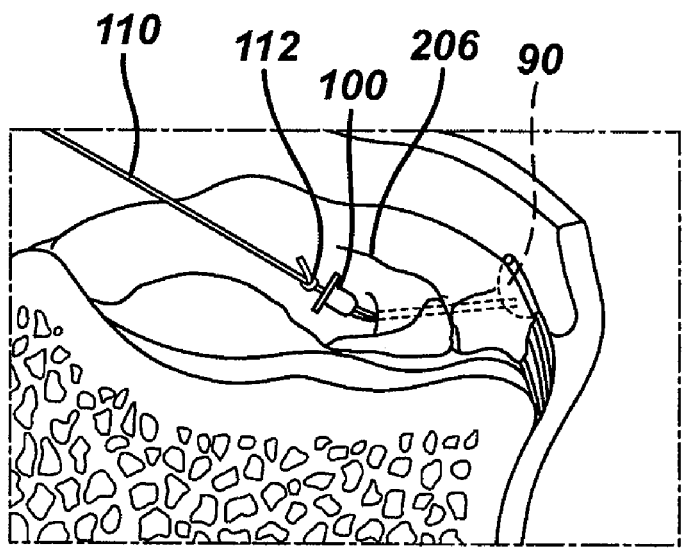

Connecting suture 110 can be tied in a slip knot to attach tissue implant 100 to the outer wall anchor 90. As shown in FIG. 8C, cannulated needle 122 is extended through the meniscus tear 206 to the outside wall 204 of the meniscus 200, whereupon the push rod 124 of inserter tool 120 is actuated and outer wall anchor 90 ejected from the cannulated needle 122 through to the outer wall 204 of the meniscus 200. Inserter tool 120 is then removed, leaving the anchor 90 against outer wall 204 with suture 110 extending through the meniscus tear 206 as illustrated in FIG. 8F. The limb of the connecting suture 110 can be pulled to assure capture and fixation of the outer wall anchor 90.

Figure 8G:
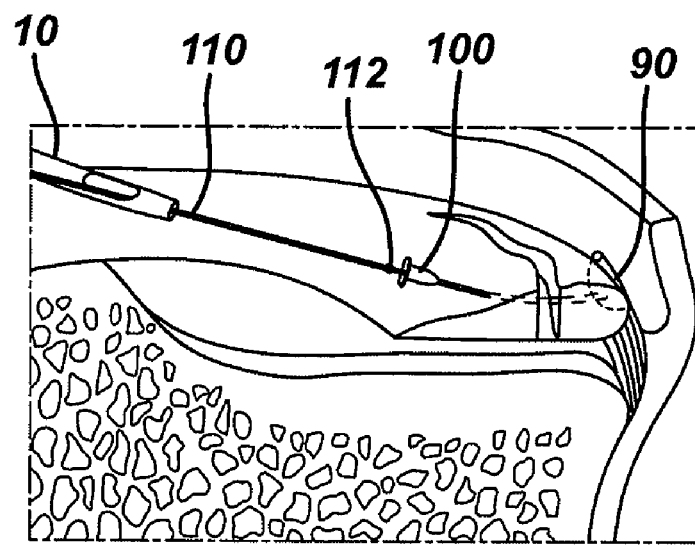
Figure 8H:
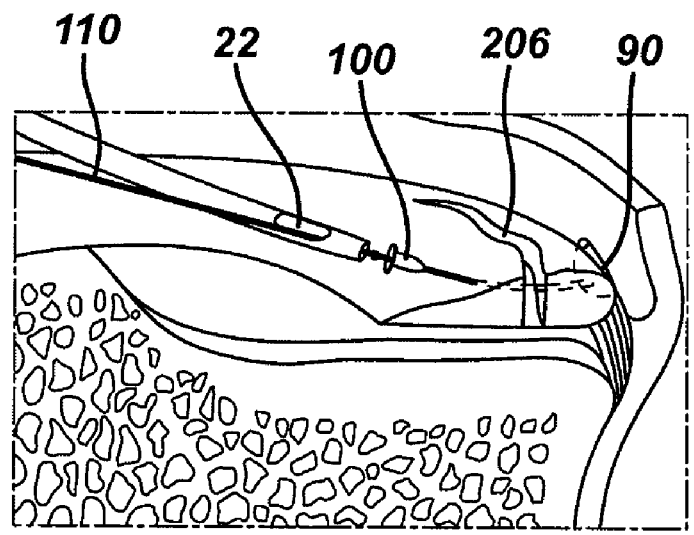
Figure 8I:
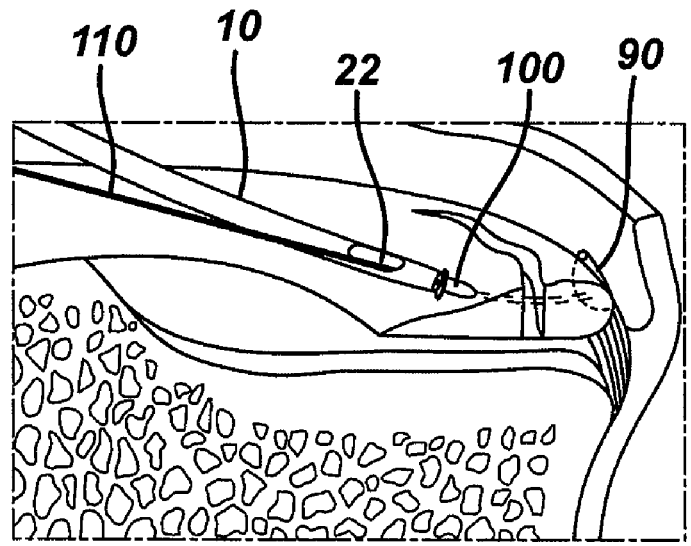
Figure 8J:
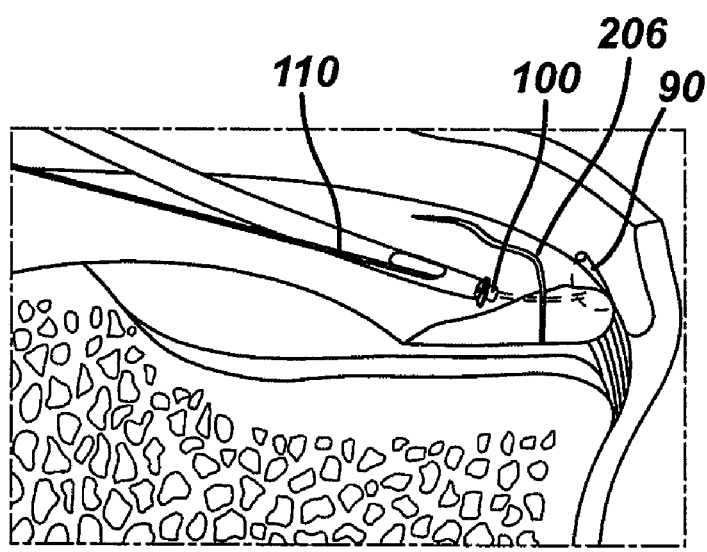

The free end of connecting suture 110 can then be threaded through conical opening 28 and the central channel 26 of the surgical knot pusher device 10, exiting out from the channel 26 to groove 22 as shown in FIG. 8G. Contoured groove 22 enables the surgeon to rest the leg of the connecting suture 60 against the groove 22 and along the length of the elongate body 16 without significantly affecting the overall diameter of the device 10 or encumbering the workspace of the surgeon. In FIG. 8H, distal tip 18 of device 10 is placed against the slip knot 112 such that about 50% of the knot 62 is surrounded by conical opening 28. Using gentle pressure while holding the leg of suture 110 taut against the device 10, the surgeon can initiate a pulling/pushing action to slide the surgical knot pusher device 10 towards the tissue implant 100, until the slip knot 112 moves down the suture strand 110 and against the tissue implant 100, as in FIG. 8I. Slightly more pressure should be applied to pull the connecting suture 110 than is applied to the pusher device 10. This will prevent the accumulation of slack in the connecting suture 110, allowing the tissue implant 100 and slip knot 112 to slide smoothly.

Figure 8K:
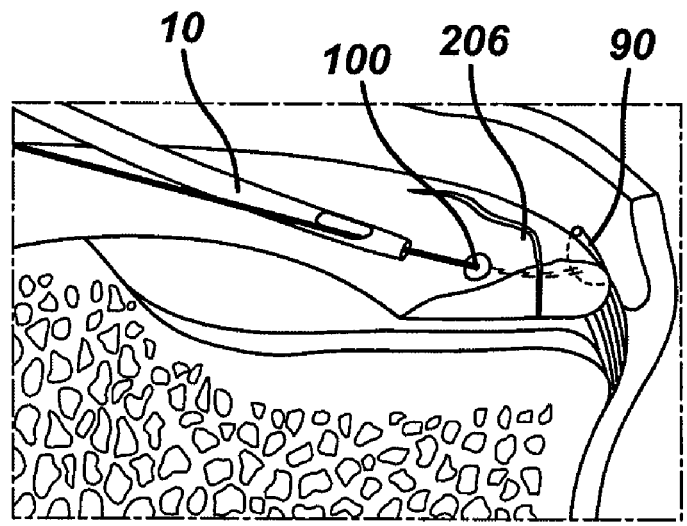

The limb of the connecting suture 110 should continue to be pulled to advance the slip knot 112 and the tissue implant 100 down to the inner wall 202 of the meniscus 200. The tissue implant 100 should be seated snugly, i.e., "dimpled" into the inner wall 202 of the meniscus 200, and the slip knot 112 abutting the top surface 104 of the implant 100, as shown in FIG. 8K. Tension should continue to be applied to the connecting suture 110 with the pusher device 10 until the slip knot 112 is tightened. The slip knot 112 can then be lodged in the through-hole 106 of the tissue implant 100 by applying pressure against the slip knot 112 with the pusher device 10. With tension on the connecting suture 110, the outer wall anchor 90 provides support against the outer wall 204. As the connecting suture 110 tightens, anchor 90 acts as a pulley, enabling the connecting suture 110 to pull the tissue surrounding the meniscus tear 206 together to promote healing of the meniscus 200.

Figure 8L:
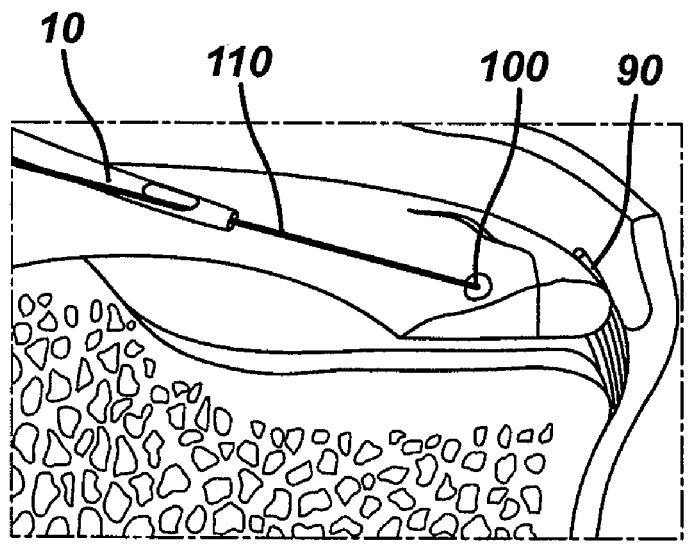
Figure 8M:
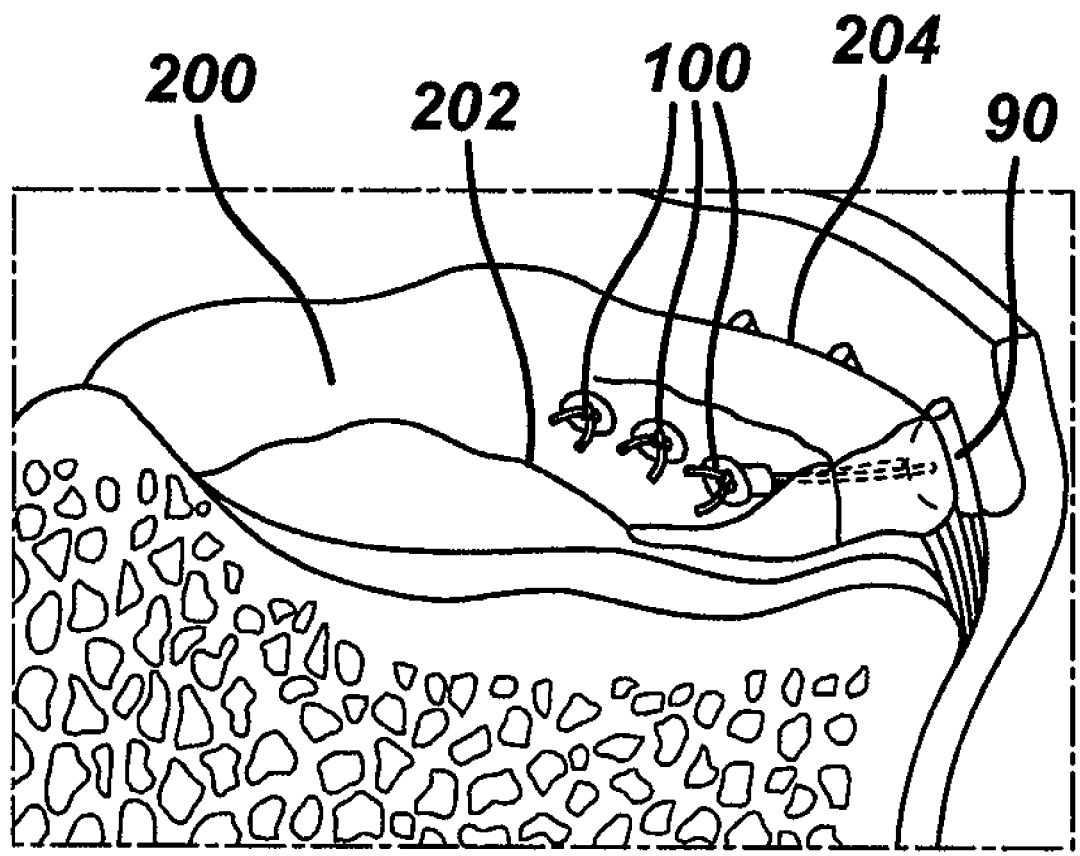

Typically the knot-engaging tissue implant 100 is formed from a pliable and resilient material having a configuration that enables knot 112 to become lodged therein. By exerting force on the distal tip 18 of device 10, the surgeon can force the tissue implant 90 into the inner wall 202 of the meniscus 200. As seen in FIGS. 8K and 8L, once the tissue implant 90 is pushed firmly against the inner wall 202 of the meniscus 200, and the slip knot 112 tightened, the device 10 can be retracted. The connecting suture 110 is then cut with an arthroscopic cutter (not shown) to leave approximately about 2 mm of suture length. As shown in FIG. 8M, the above procedure can be repeated until the desired amount of sutures is placed across the meniscus tear 206. Finally, when the procedures are complete, the meniscus 200 is probed to assure a stable repair.

While the present invention is described for use with a slip knot, it is contemplated that the pusher 10 can be utilized with any type of surgical knot. Further, the pusher 10 can be effective in surgical procedures other than tissue repairs, the pusher 10 being effective for knot pushing in any surgical procedure requiring suturing.

It will be understood that the foregoing is only illustrative of the principles of the invention, and that various modifications can be made by those skilled in the art without departing from the scope and spirit of the invention. All references cited herein are expressly incorporated by reference in their entirety.

What is claimed is:

1. A surgical knot pusher device, comprising:
a handle portion and an elongate body extending from the handle portion, the elongate body having a tapered distal tip, the distal tip having a groove formed in a portion thereof and having a radially enclosed central channel extending long a longitudinal axis of the distal tip from the groove to a distal end of the distal tip,
wherein the central channel is formed by a radiused wall at a proximal end thereof and a section in the shape of a cone at a distal end thereof with a depth that is about twice a diameter of the central channel such that the section in the shape of a cone is sized to protect a prepared knot on a leg of suture to allow it to be pushed down the leg of the suture without deforming or collapsing the knot.

2. The device of claim 1, wherein the handle portion further includes at least one finger engaging loop.

3. The device of claim 1, wherein the distal tip extends from the elongate body at an angle of up to approximately 35°.

4. The device of claim 1, wherein the groove is formed proximally of the distal end of the distal tip.

5. The device of claim 1, wherein the channel is substantially centrally disposed within the distal tip.

6. The device of claim 5, wherein the section in the shape of a cone of the central channel comprises a flared conical opening near the distal end of the distal tip.

7. The device of claim 1, wherein the groove has a contoured surface adapted for seating a portion of the suture.

8. The device of claim 1, further being formed from a rigid metal or plastic.

9. The device of claim 1, further being formed from a malleable metal or plastic.

10. The device of claim 1, wherein the section in the shape of a cone has a taper angle of approximately 41 degrees.

11. The device of claim 1, wherein the section in the shape of a cone has a depth of approximately 0.047 inches.

12. The device of claim 1, wherein the distal tip is bent with respect to the elongate body at an angle of approximately 12 degrees to approximately 35 degrees.

13. The device of claim 1, wherein a proximal surface of the groove is oriented at an angle with respect to the channel of approximately 27 degrees to approximately 33 degrees.

* * * * *